United States Patent [19]
Kouda et al.

[11] Patent Number: 6,017,740
[45] Date of Patent: Jan. 25, 2000

[54] PROCESS FOR THE PRODUCTION OF BACTERIAL CELLULOSE

[75] Inventors: Tohru Kouda; Takaaki Naritomi; Hisato Yano; Fumihiro Yoshinaga, all of Kawasaki, Japan

[73] Assignee: Bio-Polymer Research Co., Ltd., Kawasaki, Japan

[21] Appl. No.: 08/836,986

[22] PCT Filed: Aug. 30, 1996

[86] PCT No.: PCT/JP96/02454

§ 371 Date: Aug. 7, 1997

§ 102(e) Date: Aug. 7, 1997

[87] PCT Pub. No.: WO97/12987

PCT Pub. Date: Apr. 10, 1997

[51] Int. Cl.[7] .............................. C12P 19/04; C12N 1/20; C08B 1/00
[52] U.S. Cl. ....................... 435/101; 435/252.1; 435/822; 435/823; 536/56
[58] Field of Search ................................. 435/101, 252.1, 435/822, 823; 536/56

[56] References Cited

U.S. PATENT DOCUMENTS

| 4,863,565 | 9/1989 | Johnson et al. .......................... 162/150 |
| 5,079,162 | 1/1992 | Ben-Bassat et al. ................. 435/252.1 |

FOREIGN PATENT DOCUMENTS

| 7-039386 | 2/1995 | Japan . |
| 8-033495 | 2/1996 | Japan . |
| 8-205884 | 8/1996 | Japan . |

OTHER PUBLICATIONS

Watanabe et al. Biosci. Biotech. Biochem. vol. 59(1), pp. 65–68, 1995.

Toyosaki et al. Biosci. Biotech. Biochem. vol. 59(8), pp. 1498–1502, 1995.

Kouda et al. J. Ferm. Bioeng. vol. 84(2), pp. 124–127, 1997.

*Primary Examiner*—Leon B. Lankford, Jr.
*Assistant Examiner*—Christopher R. Tate
*Attorney, Agent, or Firm*—Oblon, Spivak, McClelland, Maier & Neustadt, P.C.

[57] ABSTRACT

The present invention relates to a process for the production of cellulosic material which comprises culturing a cellulose-producing bacterium while maintaining the internal pressure within the fermentation tank at about 1.1 kg/cm$^2$ A or more, preferably at about 1.2 kg/cm$^2$ A or more, more preferably at about 1.5 kg/cm$^2$ A or more, generally in the later stage of the cultivation (the growth decline phase and stationary phase), namely, at the stage where a concentration of the cellulosic material in a culture medium reaches about 10 g/L or more, preferably about 12 g/L or more; at the culturing stage where an apparent density of the culture medium at 10 rad/s or 1 l/s reaches about 10 Pa.s or more; at the culturing stage where the K value (consistency index) reaches about 10 Pa.s$^n$ or more considering that rheology follows the Power law model; or at the stage where the oxygen-demand of the culture medium reaches about 35 mmol/L.hr or more.

4 Claims, 1 Drawing Sheet

PROCESS FOR THE PRODUCTION OF BACTERIAL CELLULOSE

TECHNICAL FIELD

This invention relates to a process for the production of cellulosic material (bacterial cellulose: "BC"), which comprises using microorganisms capable of producing the BC (cellulose-producing bacteria) while maintaining the internal pressure within a fermentation tank at a certain level or above, or maintaining $CO_2$ pressure in a gas phase at a certain level or less.

BACKGROUND ART

Since the BC is edible, it is utilized in the food industry. The BC's high dispersibility in water further provides it with a lot of industrial utility value, such as to maintain viscosity of food, cosmetics or coating agents, to strengthen food materials, to maintain moisture, to improve stability of food, and to be used as low-calorie additives and an emulsion stabilizer.

The BC is characterized by a sectional width of its fibrils, which is smaller by two orders of magnitude than that of other kinds of cellulose such as those derived from wood pulp.

Due to such structural and physical features of microfibrils, a homogenized BC has plenty of industrial utility as a strengthening agent for polymers, especially hydrophilic polymers. Products prepared by solidification of the homogenized BC in the form of a lump or paper show a high elastic modulus in tension due to the above feature, and are therefore expected to have excellent mechanical properties for use in various kinds of industrial materials.

Methods for the production of the BC are described in, for example, Japanese Patent Laid-Open Application Sho 62(1987)-265990, Japanese Patent Laid-Open Application Sho 63(1988)-202394 and Japanese Patent Publication Hei 6(1994)-43443.

As a nutrient medium suitable for the culture of the cellulose-producing bacteria, Schramm/Hestrin medium is known, which contains carbon source, peptone, yeast extract, sodium phosphate and citric acid (Schramm et al., J. General Biology, 11, pp.123–129, 1954). Further, it has been found that the productivity of the BC is increased by the addition of an accelerator for the cellulose production such as inositol, phytic acid and pyrroloquinoline quinone (PQQ) (Japanese Patent Publication Hei 5(1993)-1718; Mitsuo TAKAI, Japan TAPPI Journal, Vol.42, No.3, pp.237–244), carboxylic acid or their salts (Japanese Patent Application Hei 5(1993)-191467; Japanese Patent Laid-Open Application Hei 7(1995)-39386), invertase (Japanese Patent Application Hei 5(1993)-331491; Japanese Patent Laid-Open Application Hei 7(1995)-184677) and methionine (Japanese Patent Application Hei 5(1993)-335764; Japanese Patent Laid-Open Application Hei 7(1995)-184675) into such a nutrient medium. Furthermore, a method for cultivating the cellulose producing bacteria under the specific range of oxygen-transfer coefficient ($K_L a$) condition has been proposed (Japanese Patent Application Hei 7(1995)-31787).

The bacteria may be generally cultured in any known culture conditions such as static culture, shaken culture, and aerated and agitated culture, and in any known culture operation methods such as batch fermentation, fed batch fermentation, repeated batch fermentation and continuous fermentation.

Means for agitation include impellers (agitating blades), air-lift fermenters, pump-driven recirculation of the fermenter broth and any combination of these means.

The impellers include gate-shape impellers, turbine impellers, double helical ribbon impellers and screw impellers.

The productivity in the culture of bacteria has been generally improved by the increment of the inner pressure within the fermentation tank, followed by the increment of an oxygen-supply into a culture medium.

The above advantage may be contributed to the increment of a partial pressure of $O_2$ in the gas phase (air bubbles), which will cause the increment of oxygen-transfer according to the following formula:

$$dC_L/dt = K_L a\ (C^* - C_L) = H\ K_L a\ (P_G - P_L)$$

wherein $dC_L/dt$: Oxygen-transfer rate (mmol/L.hr)

$K_L a$: Oxygen-transfer coefficient ($hr^{-1}$);

$C_L$: Dissolved oxygen concentration in the culture medium (mmol/L);

$C^*$: Dissolved oxygen concentration (mmol/L) which is in an equilibrium state with the partial pressure of oxygen in the air bubbles;

$H$: Henry's constant;

$P_G$: Partial pressure of oxygen in the gas phase; and $P_L$: Partial pressure of oxygen in the liquid phase.

However, the effect of the internal pressure within the fermentation tank on the BC production has not yet been clarified.

In the prior BC production methods, accumulation of the BC in the culture medium due to the culture of the cellulose-producing bacteria will increase the viscosity of the culture medium and make it difficult to transfer oxygen into the culture medium, so that the increment of an agitation rate or an amount of aeration was needed to fulfill the necessary amount of oxygen-supply. However, these prior methods are not economical since they need much power. Up to now, the shape of impellers and fermentation tank has been improved (Japanese Patent Application Hei 7(1995)-31787). However, it has not yet examined in detail whether or not the increment of the internal pressure within the fermentation tank may secure the necessary amount of the oxygen-supply.

The present inventors have studied an improvement in the oxygen-supply which may be easily obtained without any specialized facilities, and now found that the power required for agitation to fulfill the oxygen-supply may be remarkably reduced by the increment of the pressure under the specific conditions.

No report has been made concerning the effect of $CO_2$ concentration on the productivity of BC during culture. The present inventors have now found that the BC production rate and yield may be increased by maintaining the partial pressure of $CO_2$ in the gas phase within the fermentation tank below a certain level.

The present invention has been completed on the basis of the above findings.

DISCLOSURE OF INVENTION

The present invention relates to a process for the production of cellulosic material which comprises culturing a cellulose-producing bacterium while maintaining the internal pressure within the fermentation tank at about 1.1 kg/cm² A or more, preferably at about 1.2 kg/cm² A or more, more preferably at about 1.5 kg/cm² A or more, generally in the later stage of the cultivation (the growth decline phase and stationary phase), namely, at the stage where a concentration of the cellulosic material in a culture medium reaches about 10 g/L or more, preferably about 12 g/L or more; at the culturing stage where an apparent density of the culture medium at 10 rad/s or 1 l/s reaches about 10 Pa.s or more; at the culturing stage where the K value (consistency index) reaches about 10 Pa.s$^n$ or more considering that rheology follows the Power law model; or at the stage where the oxygen-demand of the culture medium reaches about 35 mmol/L.hr or more.

The "internal pressure within the fermentation tank" means the pressure of the gas phase within the fermentation tank, supposing that the atmospheric pressure is 1 kg/cm$^2$ A.

The internal pressure within the fermentation tank may be maintained above the certain level during the whole cultivation stage, not being especially limited to the above stages.

The maintenance of the internal pressure within the fermentation tank above the certain level may be carried out by means of very convenient methods which are well known to those skilled in the art, such as controlling an exhaust valve.

The present invention also relates to a process for the production of cellulosic material which comprises culturing a cellulose-producing bacterium, while maintaining the partial pressure of $CO_2$ in the gas phase within the fermentation tank at about 0.10 atm or less, preferably at about 0.08 atm or less.

The partial pressure of $CO_2$ may be maintained below the certain level during the whole cultivation stage, generally being preferably maintained at the later stage of the cultivation.

The partial pressure of $CO_2$ may be actually reduced to the certain level by, for example, increasing the amount of aeration into the fermentation tank or recycling the gas phase to a $CO_2$-absorbing tower.

It will be preferable to simultaneously maintain both the internal pressure within the fermentation tank below the certain level and the partial pressure of $CO_2$ below the certain level.

In addition to the above culture conditions and culture operation methods, it is also possible to use for the present invention the method for the production of BC described in the Japanese Patent Application Hei 6(1994)-192287 (Japanese Patent Laid-Open Application Hei 8(1996)-33494), wherein culture media containing bacteria are circulated between a cultivating apparatus and a separator such as a floatation equipment and an edge filter to separate the resulting BC from the bacteria and culture media in said separator.

The cellulose-producing bacteria used in the present invention include Acetobacter strains such as *Acetobacter xylinum* subsp. sucrofermentans such as BPR 2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; Agrobacterium; Rhizobium; Sarcina; Pseudomonus, Achromobacter; Alcaligenes; Aerobacter; Azotobacter; and Zooglea; and strains derived from those strains by using known mutagens such as NTG (nitrosoguanidine).

The BPR 2001 was deposited at the National Institute of Bioscience and Human-Technology Agency of Industrial Science and Technology on Feb. 24, 1993 under accession number FERM P-13466, and then transferred on Feb. 7, 1994 to the deposit under the terms of the Budapest Treaty on the International Recognition of the Deposit of Microorganisms for the Purposes of Patent Procedure and Regulation under accession number FERM BP-4545.

The chemical treatment using mutagens such as NTG is described in, for example, Bio Factors, Vol. 1, pp.297–302 (1988) and J. Gen. Microbiol, Vol. 135, pp.2917–2929 (1989). Accordingly, those skilled in the art may obtain the present mutants in accordance with these known methods. The present mutants may be also obtained by other treatments such as application of radioactive rays.

Carbon sources in the culture media useful in the present invention include sucrose, glucose, fructose, mannitol, sorbitol, galactose, maltose, erythritol, glycerol, ethyleneglycol, ethanol and their mixtures. In addition, sucrose may be combined with starch hydrolysate containing these carbon sources, citrus molasses, beet molasses, squeezed juice from beet or sugar (cane, juice from citrus and the like.

Nitrogen sources useful in the present invention include organic or inorganic ones such as ammonium salts including ammonium sulfate, ammonium chloride, ammonium phosphate; nitrates; and urea. Nitrogen-containing natural nutrients may be also used including Bacto-Peptone, Bacto-soytone, Yeast-Extract, and Bean-Condensate.

A trace amount of organic nutrients may be further added including amino acids, vitamins, fatty acids, nucleic acids, 2,7,9-tricarboxy-1H pyrrolo[2,3,5]-quinoline-4,5-dione, sulfite pulp waste liquor, lignin sulfonic acid and the like.

When the mutants with nutritional requirement for amino acids are used, such required nutrients should be supplemented in the culture media. Inorganic nutrients include phosphate salts, magnesium salts, calcium salts, iron salts, manganese salts, cobalt salts, molybdate salts, hematite salts, chelate metal salts and the like.

It is also possible to optionally supply the known accelerators for the cellulose production.

For example, when the Acetobacter is used as the cellulose-producing bacteria, a pH range for the culture is controlled between 3 and 7, preferably around 5. A culture temperature is kept in a range between 10 and 40° C., preferably between 25 and 35° C. Oxygen supply into a cultivating apparatus may contain from 1 to 100% oxygen, desirably 21 to 80%. Those skilled in the art may optionally determine the contents of these components in the culture media and the inoculation of the bacteria into the media, depending on the culture method to be used.

The BC produced in the present method may, be recovered together with the bacterial cells, and then impurities other than the BC, including the bacterial cells per se, may be removed from the recovered BC.

The impurities may be almost completely removed from the BC by washing, dehydration under pressure, dilute acid washing, alkali washing, bleaching with hypochlorite soda or hydrogen peroxide, lysing with lytic enzymes such as lysozyme, treatment with surfactants such as lauryl sulfate soda or deoxycholate soda, washing under heat at a temperature range between a room temperature and 200° C., and any combination of these treatments.

The BC thus obtained according to the present invention includes cellulose, those comprising heteropolysaccharides having cellulosic main chains, and those comprising β-1,3- or β-1,2-glucan. Said heteropolysaccharides contain as components hexoses, pentoses and organic acids such as mannose, fructose, galactose, xylose, arabinose, rhamnose and glucuronic acid, as well as glucose.

These polysaccharides may be present alone or as a mixture combined each other via hydrogen bonds.

Measurement of Viscosity

Viscosity (complex viscosity) is measured by a dynamic liquid visco-elasticity method or static method by means of a plane disk-rotating rheometer "FLUID SPECTROMETER RFS-II" (Rheometrics CO., Ltd.). The measurement is carried out in a range from 1 to 100 rad/s and from 1 to 10 l/s. Distortion ratio is 10% in the dynamic liquid visco-elasticity method. An apparent viscosity is measured from stresses under each shearing condition, and the apparent viscosities measured at 10 rad/s or 1 l/s are considered representative values. The viscosity characteristics of the culture medium containing BC is considered to follow the Power law model in the measuring range and represented as the following formula:

$$\eta_{ap} = K|\dot{\gamma}|^{(n-1)}$$

wherein $\eta_{ap}$ Pa.S is an apparent viscosity, K is consistency index Pa.S$^n$, $\gamma$ S$^{-1}$ is an average shearing rate, n is Power law index (–). "n" is determined so that a range of deviation in the value "K" may be minimized.

Measurement of the Amount of Oxygen-Demand

The amount of oxygen-demand in the culture medium is measured on the basis of the difference between the oxygen concentration in aeration gas and in exhaustion gas. That is, the amount of oxygen-consumption is calculated by multiplying the aeration amount by the above difference and dividing the thus obtained consumption amount by the volume of culture medium. Since the oxygen concentration in aeration gas and the dissolved oxygen concentration in the culture medium are constantly maintained, and the oxygen is saturated in the medium, the amount of oxygen-demand may be deemed to be the same as the amount of oxygen-consumption.

Measurement of the Internal Pressure Within the Fermentation Tank and Partial Pressure of $CO_2$ in the Gas Phase These values may be measured according to the conventional methods in the art. For example, the internal pressure within the fermentation tank is measured by a diaphragm pressure meter directly placed into the tank. The $CO_2$ concentration may be measured with a nondispersive infrared absorption apparatus connected on-line into the exhaustion gas. The partial pressure of $CO_2$ may be obtained by multiplying the $CO_2$ concentration by the internal pressure within the fermentation tank.

BEST MODE FOR CARRYING OUT THE INVENTION

Figure 1:
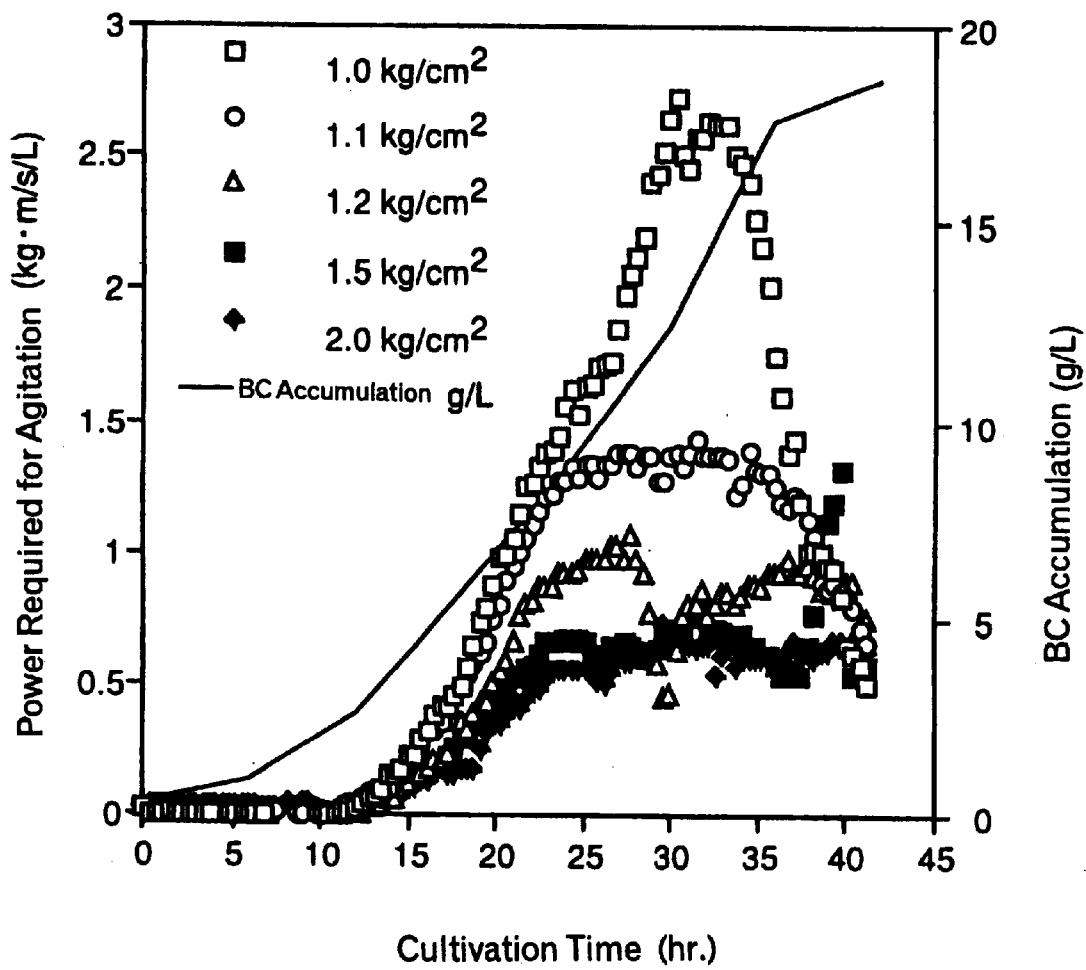
FIG. 1 shows the changes in the power required for agitation and accumulation of BC during the course of time.

The present invention will be further illustrated according to the following examples.

EXAMPLE 1

BPR 3001A strain which is a mutant derived from the BPR 2001 strain and deposited on Jun. 12, 1995 under accession number FERM P-14982 was cultured under the following conditions.

Cultivating Condition

A jar fermentor (50 liter volume) containing 30 liter of CSL-Fru medium which has been sterilized therein was used as a cultivating apparatus. The jar fermentor was inoculated with the bacteria cultured in a Roux flask or conical flask, and cultured at 30° C. for about 40 hours. The viscosity of the culture medium was measured by the dynamic liquid visco-elasticity method using a removed culture medium. The oxygen concentration in aeration and exhaust gas was measured by means of an on-line oxygen concentration meter. The required power was measured on the basis of the power of the inversion out-put of an agitation motor.

Composition of Culture Medium

TABLE 1

| CSL-Fru medium | | |
| --- | --- | --- |
| Fructose | 7.0 | (%) |
| KH$_2$PO$_4$ | 0.1 | |
| MgSO$_4$.7H$_2$O | 0.025 | |
| (NH$_4$)$_2$SO$_4$ | 0.33 | |
| Vitamin Mixture (see below) | 1.0 | |
| Salt Mixture (see below) | 1.0 | |
| CSL (Corn Steep Liquor) | 4.0 | |
| pH | 5.0 | |

TABLE 2

| Vitamin Mixture | |
| --- | --- |
| compound | mg/L |
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

TABLE 3

| Salt Mixture | |
| --- | --- |
| Iron Citrate Ammonium | 360 mg/L |
| Calcium Chloride | 1470 mg/L |
| Ammonium Molybdate | 242 mg/L |
| Zinc Sulfate Heptahydrate | 173 mg/L |
| Manganese Sulfate Tetrahydrate | 139 mg/L |
| Copper Sulfate Pentahydrate | 5 mg/L |

The changes in the power required for agitation and accumulation of BC during the course of time are shown in FIG. 1.

The results in FIG. 1 demonstrate that under the conditions of BC concentration (accumulation) of 10 g/L or more after 24 hours in the cultivation course of time, the maximum of the required power was reduced by about 50% at 1.1 kg/cm$^2$A, by about 38% at 1.2 kg/cm$^2$A, and by about 25% at 1.5 kg/cm$^2$A, respectively, against that at 1 kg/cm$^2$A of the internal pressure within the fermentation tank. There reduction rates were remarkably larger than those expected on the basis of the above formula.

EXAMPLE 2

By using the same cultivating apparatus and medium as in Example 1, the production rate and yield of BC were obtained, varying the rate of agitation, the amount of aeration, and the internal pressure within the fermentation tank. The results are shown in Table 4.

TABLE 4

| Aeration (vvm) | 1/4 | 1/4 | 1/2 | 1/2 | 1/1 |
|---|---|---|---|---|---|
| Max. Agitation (rpm) | 450 | 400 | 400 | 350 | 400 |
| Internal Pressure (kg/cm$^2$A) | 1.5 | 2.0 | 1.5 | 2.5 | 1.5 |
| Max. CO$_2$ Partial Pressure (atm) | 0.12 | 0.16 | 0.06 | 0.10 | 0.03 |
| Production rate (g/L · h) | 0.38 | 0.37 | 0.44 | 0.41 | 0.44 |
| Yield (%) | 23 | 22 | 26 | 25 | 26 |

The accumulated amounts of the BC (g/L) in respective Figure were calculated as follows. After the completion of the culture, the solid contents in the jar fermenter were collected, washed with water to remove the medium components, and treated with 1 N NaOH aqueous solution at 80° C. for 20 minutes to remove the bacterial cells. The resulting cellulose was washed until the washing water became approximately neutral, and dried under vacuum at 80° C. for 12 hours to weigh the dry cellulose. The yield against the consumed sugars (%) was calculated as follows.

Calculation of Yield Against the Consumed Sugars (%)

$$Y_{BC} = BC/(RC_{MF} - RC_{BF}) * 100$$

$Y_{BC}$: Yield against the consumed sugars (%)

BC: Accumulated amount of BC (g/L)

$RC_{MF}$: Sugar concentration of the medium (g/L)

$RC_{BF}$: Sugar concentration of the medium after the culture (g/L)

INDUSTRIAL APPLICABILITY

According to the present invention, the power required for agitation during the cultivation for the production of BC may be remarkably reduced, and the BC production rate and yield may be increased.

What is claimed is:

1. A process for the production of bacterial cellulose, which comprises culturing a cellulose-producing bacterium within an aerated and agitated fermentation tank while maintaining the partial pressure of $CO_2$ in the gas phase within the fermentation tank at about 0.10 atm or less substantially throughout the later stage of cultivation, wherein the later stage of cultivation comprises the growth decline phase and stationary phase of the cultivation.

2. A process for the production of bacterial cellulose, which comprises culturing a cellulose-producing bacterium within a fermentation tank while maintaining the partial pressure of $CO_2$ in the gas phase within the fermentation tank at about 0.10 atm or less during the stationary phase and growth decline phase of cultivation when the concentration of bacterial cellulose in the culture medium reaches about 10 g/L or more.

3. A process for the production of bacterial cellulose, which comprises culturing a cellulose-producing bacterium within a fermentation tank while maintaining the partial pressure of $CO_2$ in the gas phase within the fermentation tank at about 0.10 atm or less during the stationary phase and growth decline phase of cultivation when the apparent density of the culture medium at 10 rad/s or 1 1/s reaches about 10 Pa.s or more; or when the culturing stage where the K value (consistency index) reaches about 10 Pa.s$^n$ or more considering that rheology follows the Power law model.

4. A process for the production of bacterial cellulose, which comprises culturing a cellulose-producing bacterium within a fermentation tank while maintaining the partial pressure of $CO_2$ in the gas phase within the fermentation tank at about 0.10 atm or less during the stationary phase and growth decline phase of cultivation when the oxygen-demand of the culture medium reaches about 35 mmol/L.hr or more.

* * * * *

UNITED STATES PATENT AND TRADEMARK OFFICE
CERTIFICATE OF CORRECTION

PATENT NO. : 6,017,740

DATED : January 25, 2000

INVENTOR(S): Tohru KOUDA et al.

It is certified that an error appears in the above-identified patent and that said Letters Patent is hereby corrected as shown below:

On the title page, item [30] has been omitted. It should be:

--[30] Foreign Application Priority Data

Sep. 29, 1995 [JP] Japan.........7-276408--

Signed and Sealed this

Third Day of April, 2001

Attest:

NICHOLAS P. GODICI

Attesting Officer     Acting Director of the United States Patent and Trademark Office